United States Patent [19]
DeSatnick et al.

[11] Patent Number: 5,772,664
[45] Date of Patent: Jun. 30, 1998

[54] INSTRUMENT FOR HARVESTING BONE GRAFTS HAVING SUBSTANTIALLY CYLINDRICAL BONE PLUGS

[75] Inventors: Allen H. DeSatnick; Ella Zaslavsky, both of Marblehead; Herbert Marcus, Chelmsford, all of Mass.

[73] Assignee: Wright Medical Technology, Inc., Arlington, Tenn.

[21] Appl. No.: 798,108

[22] Filed: Feb. 12, 1997

[51] Int. Cl.[6] .................................................. A61B 17/56
[52] U.S. Cl. .............................. 606/80; 606/79; 408/204
[58] Field of Search .................................. 606/79, 80, 81, 606/82, 83, 84, 85, 86, 96; 408/203.5, 204

[56] References Cited

U.S. PATENT DOCUMENTS

| | | | |
|---|---|---|---|
| 4,306,570 | 12/1981 | Matthews | 128/754 |
| 4,573,838 | 3/1986 | Omi et al. | 408/204 |
| 4,669,931 | 6/1987 | Isaksson | 408/206 |
| 5,054,971 | 10/1991 | Kieninger et al. | 408/205 |
| 5,205,685 | 4/1993 | Herbert | 408/204 |
| 5,316,416 | 5/1994 | Kim | 408/145 |
| 5,490,853 | 2/1996 | Burkinshaw et al. | 606/79 |
| 5,556,399 | 9/1996 | Huebner | 606/80 |
| 5,613,972 | 3/1997 | Lee et al. | 606/107 |
| 5,632,747 | 5/1997 | Scarborough et al. | 606/79 |

FOREIGN PATENT DOCUMENTS 2 678 500 A1   1/1993   France.

OTHER PUBLICATIONS

Dobson, "The HTS—Helical Tube Saw—Ligament Graft Harvesting System", *Roberts Medical, Inc.*
"The HTS—Helical Tube Saw—Ligament Graft Harvesting System", *Roberts Medical, Inc.*

*Primary Examiner*—Guy V. Tucker
*Attorney, Agent, or Firm*—Lappin & Kusmer LLP

[57] ABSTRACT

An instrument and kit for harvesting a bone-patella tendon-bone (BTB) graft having substantially cylindrical bone plugs, and a method for harvesting a BTB graft. The instrument comprises two cylindrical shell portions extending along an axis from a drive end to a cutting end. One of the shell portions, which is positionable around a portion of the tendon, includes an axial slot which permits the graft portion of the tendon to extend therethrough. The shell portions interlock together in a hinged and mutually biased engagement to form a cylindrical tube around the graft portion, with a cutting edge that extends a full 360 degrees about the axis of rotation. Bone plugs obtained using the instrument are fully circular in cross-section for substantially their entire length.

12 Claims, 7 Drawing Sheets

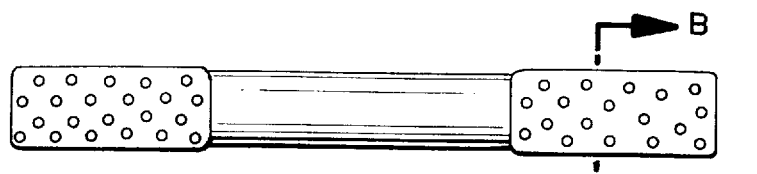 
FIG. 1A PRIOR ART  FIG. 1B PRIOR ART
 
FIG. 1C PRIOR ART  FIG. 1D PRIOR ART
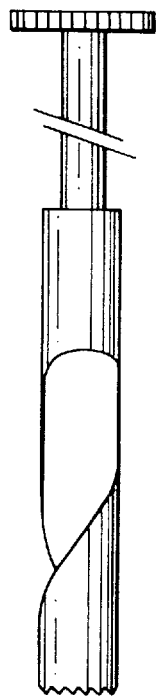
FIG. 2A PRIOR ART
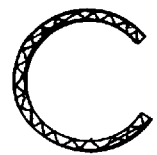
FIG. 2B PRIOR ART

 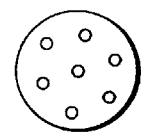
FIG. 4A  FIG. 4B
 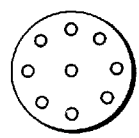
FIG. 4C  FIG. 4D
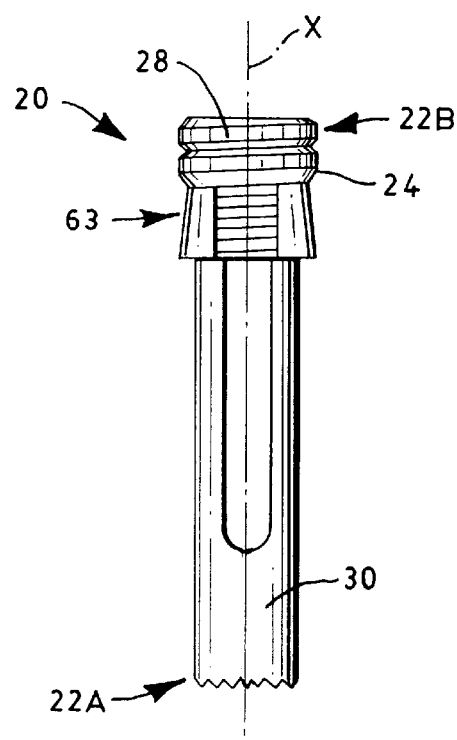 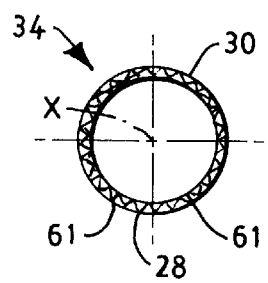
FIG. 3A  FIG. 3B

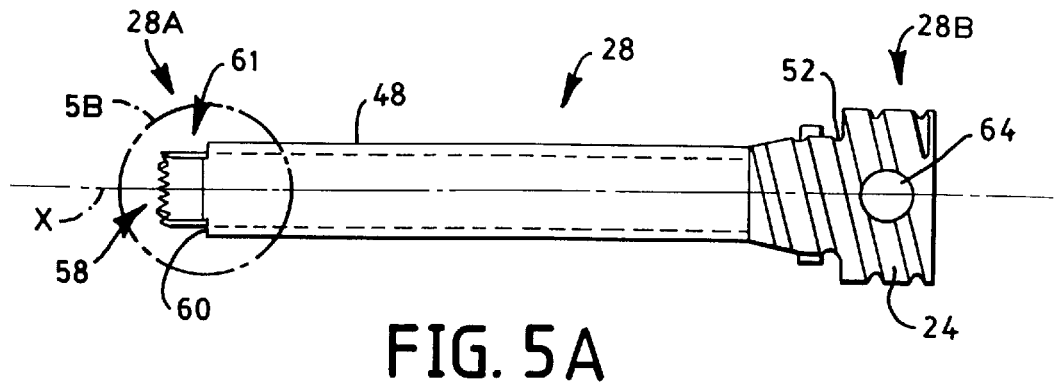
FIG. 5A
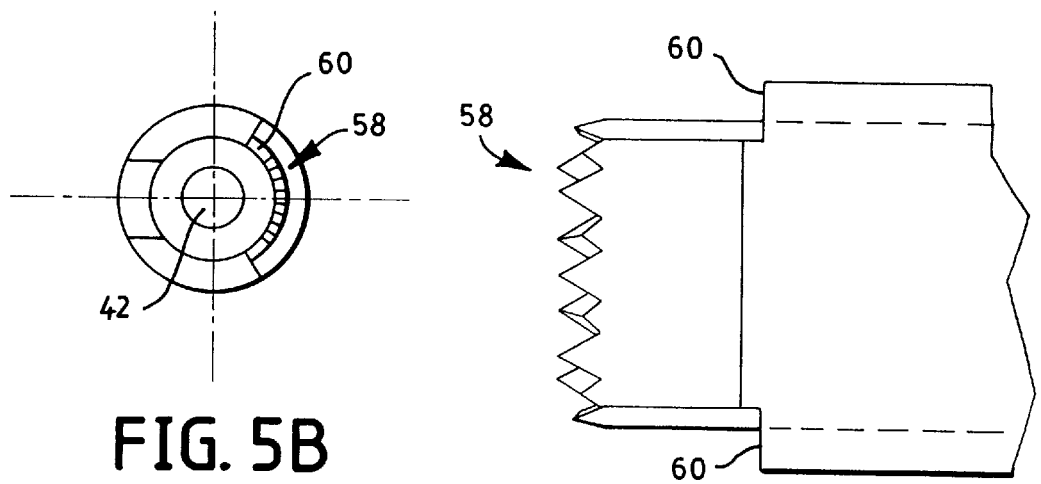
FIG. 5B
FIG. 5C
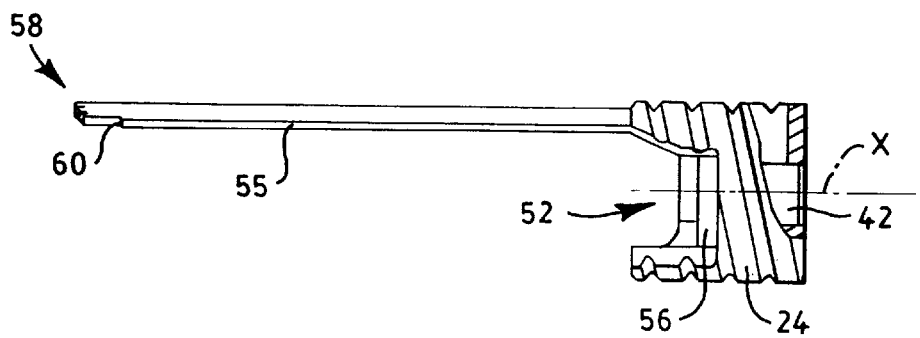
FIG. 5D

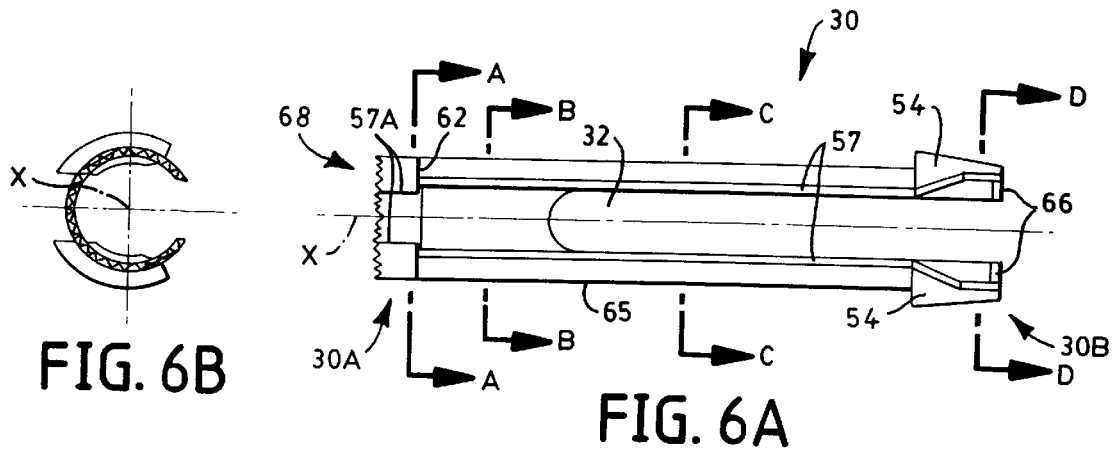
FIG. 6B
FIG. 6A
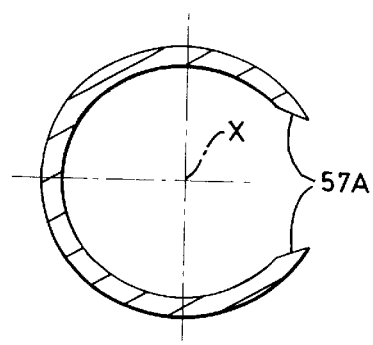
FIG. 7A
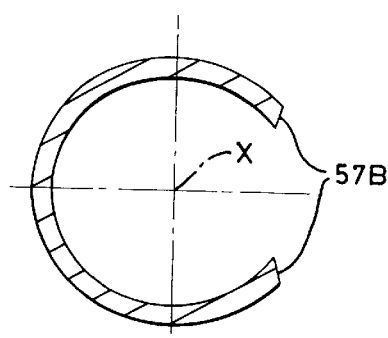
FIG. 7B
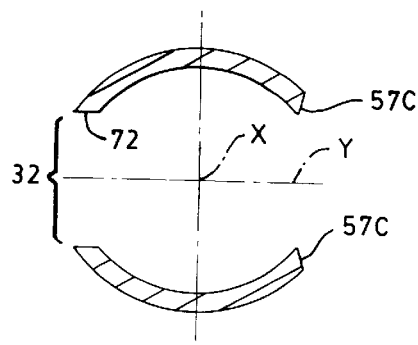
FIG. 7C
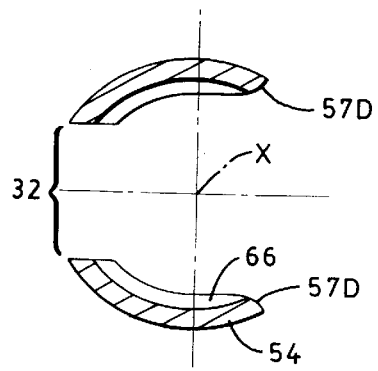
FIG. 7D

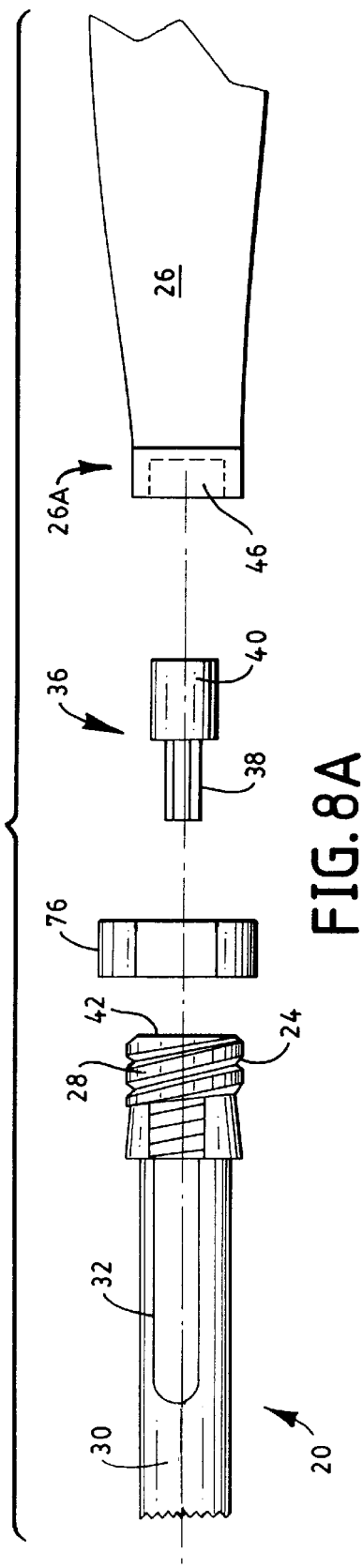
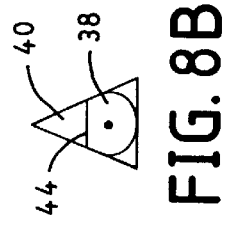
FIG. 8B
FIG. 8A
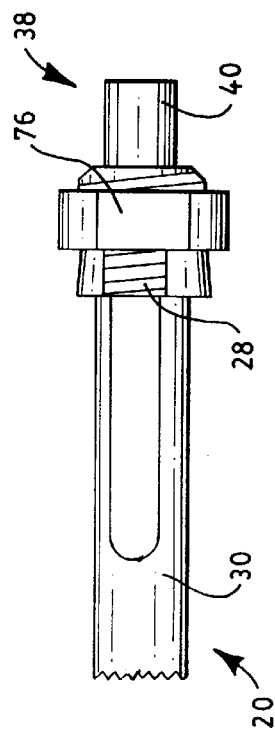
FIG. 9

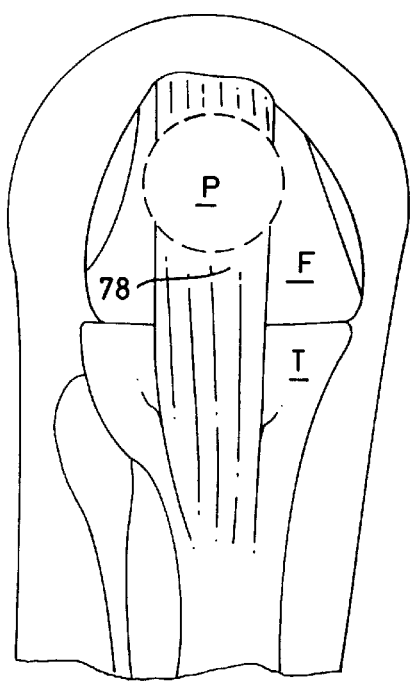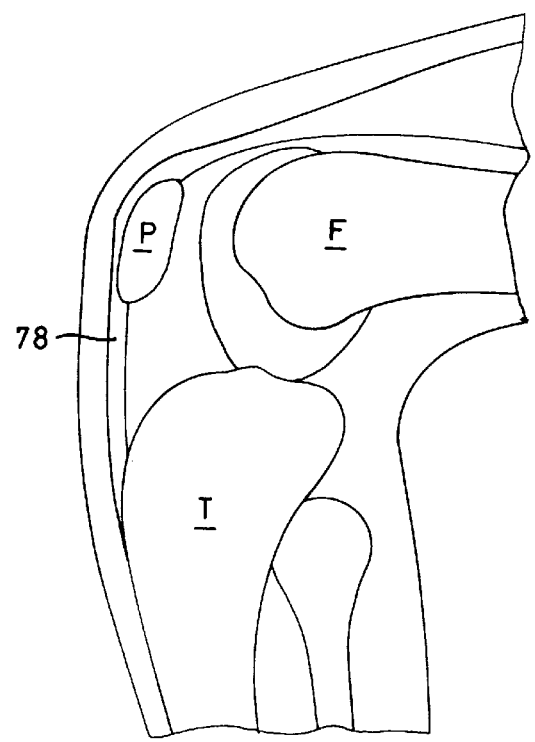
FIG. 10A  FIG.10B
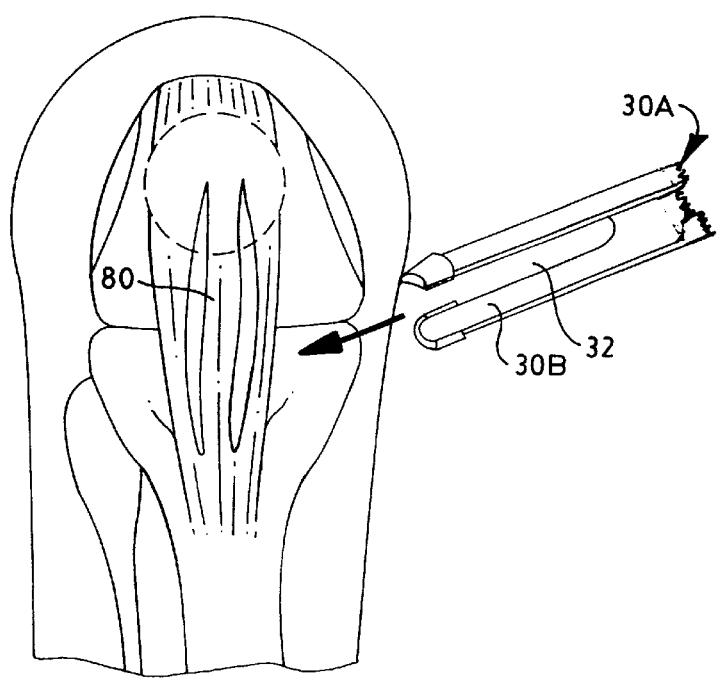
FIG. 11

INSTRUMENT FOR HARVESTING BONE GRAFTS HAVING SUBSTANTIALLY CYLINDRICAL BONE PLUGS

FIELD OF THE INVENTION

This invention relates to surgical instruments for cutting through bone, and more particularly to surgical instruments for harvesting a bone-patella tendon-bone (BTB) graft for use in the surgical reconstruction of the anterior cruciate ligament of the knee.

BACKGROUND OF THE INVENTION

Reconstruction of the anterior cruciate ligament (ACL) is most commonly effected with a patella tendon autograft (a graft obtained from the patient's own tissue) or allograft (a graft obtained from a donor). Such a graft typically comprises a section of patella tendon having less than fully cylindrical bone plugs from the patella and tibia at respective ends thereof, as shown in FIGS. 1A–1D.

A longitudinal section of the patella tendon is currently the most popular choice of surgeons for an ACL autograft. The portion of the tendon to be used for the graft, generally the middle third of the tendon as viewed frontally, is incised on both sides with a surgical knife inserted in line with longitudinally extending collagen fibers in the tendon and well away from the respective insertion points of the tendon in the patella and tibia. The bone plugs on either end of the graft section of the tendon are harvested from the patella and tibia, respectively, with chisel-like osteotomes or tubular cylindrical saws of a preselected diameter, typically 9, 10 or 11 millimeters.

Graft-receiving tunnels are drilled in appropriate locations in the tibia and femur for insertion of the bone plugs. As the tunnels are generally circular in cross-section, cylindrical bone plugs are preferred, both for ease of fit into the osseous tunnels of the tibia and femur and for maximum contact area of the bone plugs in the osseous tunnels. Greater contact area of a bone plug in an osseous tunnel promotes faster healing and better ingrowth of bone, resulting in superior fixation of the plug in the bone tunnel and thus increased graft strength and flexibility.

Cylindrical saws for the harvesting of cylindrical bone plugs are known. For example, FIGS. 2A illustrates a helical tube saw used to harvest ligament grafts, manufactured by Kaltec Property Ltd. (South Australia) and distributed by Roberts Medical, Inc. (Boyertown, PA). This relatively thick-walled device has a helical aperture extending longitudinally along the tube from the cutting end to permit a section of ligament or soft tissue to be fed into and through the tube so that it is away from the cutting surface of the saw during harvesting of a bone plug from the bone at the ligament insertion point. The helical tube is designed to be manually rotated under moderate pressure through an arc of approximately 60° degrees in an oscillatory motion to cut the bone. The tissue section being cut by the saw is partially surrounded by the helical body of the saw, and as the saw rotates, the tissue section can travel along the helical pathway cut into the tube.

Bone plugs harvested with such helical saws are less than fully cylindrical for at least a portion of their length. This is disadvantageous in that the resulting bone plugs, when implanted into the osseous tunnels, are not uniformly near or in contact with the walls of the osseous tunnels. As a result, bone ingrowth is not optimized, and therefore healing and rehabilitation may occur more slowly.

As shown in FIG. 2B, the cutting end of the helical tube saw does not extend a full 360° degrees about the axis of rotation of the saw but instead forms an open, or C-shaped, cutting edge. Because of the "C"-shaped cross-section of the cutting end of the helical tube saw, a portion of the tissue sections and bone plugs cut therewith may have a ragged edge. When a bone is cut with the helical tube saw, the discontinuity in the cutting surface may catch or seize the bone as the saw is rotated, resulting in sharp edges and a plug having a noncylindrical cross-section. When a tendon or other soft tissue section is cut, the discontinuity in the cutting surface may catch and/or drag the tissue as the saw is rotated, thus tearing or damaging it. Thus, during use, the cutting edges must always be visible on either side of the tendon to ensure that the tendon is not caught by the cutting edge as it is oscillated around the tendon.

It would therefore be an advantage in the art to provide a bone graft harvesting instrument which overcomes the deficiencies of the prior art instruments and which provides bone grafts which are superior to those obtained with prior art instruments.

OBJECTS OF THE INVENTION

It is therefore an object of the invention to provide a bone graft harvesting instrument with a cutting surface which extends fully about the axis of rotation of the instrument and still provides clearance for a section of soft tissue therein.

It is another object of the invention to provide a bone graft harvesting instrument which is made of multiple interlocking pieces which permit the graft portion of a tendon to reside within the instrument during the harvesting operation, so that the harvesting operation produces bone plugs which are fully cylindrical for substantially their entire length.

It is another object of the invention to provide a bone graft harvesting instrument which is made of multiple interlocking pieces which, when interlocked, are of similar strength to a harvesting instrument of unitary construction.

It is another object of the invention to provide a method for harvesting a BTB graft having substantially cylindrical bone plugs using the harvesting instrument of the present invention.

SUMMARY OF THE INVENTION

The bone plug harvesting instrument of the present invention is a two-piece cylindrical tube which interlockingly engages to provide a cutting edge which extends a full 360° degrees about the axis of rotation of the instrument. As a result, a bone plug of substantially circular cross-section for substantially its entire length can be obtained. The use of a harvesting instrument having such a "closed" cutting edge provides a bone plug having a smooth cylindrical shape and eliminates the risk of the soft tendinous tissue being caught or torn by an opening in the cutting edge of the harvesting instrument. In addition, the use of two interlocking pieces to form a single cylindrical tube allows the graft portion of the tendon to be disposed within the tube, thereby permitting the harvesting instrument to cut fully into the patella and the tibia from the tendon portion to obtain bone plugs which are fully circular in cross-section throughout substantially their entire length. The interlocking engagement of the two cylindrical pieces ensures that the structural integrity of the instrument is maintained during the bone graft harvesting operation.

According to one aspect of the invention, there is provided an instrument for harvesting a BTB graft having substantially cylindrical bone plugs. The instrument comprises a substantially cylindrical tube which extends along a central axis between a cutting end and a drive end. The tube includes first and second elongated interlocking detachable elements. Each of the elements includes an elongated cylindrical shell portion extending from the cutting end toward the drive end. The first and second elements, when interlocked, are biased towards each other and establish a cutting edge that extends fully about the axis. The first element includes a coupler at the drive end which is adapted for releasable engagement with a rotatable driver, which can be either manually- or power-driven. The second element includes an axially extending slot near the drive end.

The cylindrical tube further comprises a hinge element disposed near the cutting end of the tube, and a biasing element disposed between the cutting end and the drive end of the tube. The hinge element is adapted for hingedly interlocking the first and second elements together near the cutting end of the tube. The biasing element is adapted for biased engagement of the first and second elements along their respective lengths between the cutting end and the drive end of the tube.

The biasing element comprises a set of corresponding contact surfaces on the first and second elements which are adapted for biased engagement with each other to provide an interlocking engagement of the first and second elements along their respective lengths. This interlocking engagement ensures that the two elements of the cylindrical tube remain securely interlocked during operation of the harvesting instrument.

The instrument further includes a clamping element disposed near the drive end of the tube. The clamping element is adapted for releasably securing the first and second elements together near the drive end.

In one embodiment, the cutting end of the tube includes a plurality of bone-cutting teeth. In an alternate embodiment, the cutting end of the tube includes a bone-abrading surface which can include, for example, a diamond coating.

According to another aspect of the invention, there is provided a kit for harvesting a BTB graft having substantially cylindrical bone plugs. The kit comprises:

A. an instrument for harvesting a BTB graft having substantially cylindrical bone plugs, and B. a rotatable driver adapted for releasable engagement with said coupler.

The instrument comprises a substantially cylindrical tube extending along a central axis between a cutting end and a drive end. The tube includes first and second elongated interlocking detachable elements, each of which includes an elongated cylindrical shell portion that extends from the cutting end towards the drive end. The first and second elements, when interlocked, are biased towards each other and establish a cutting edge that extends fully about the axis. The first element includes a coupler at the drive end which is adapted for releasable engagement with a rotatable driver. The second element includes an axially extending slot near the drive end.

The rotatable driver is adapted for both manual- and power-driven oscillatory rotary motion.

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 1A is a plan view of a BTB graft obtained with a prior art harvesting instrument;

FIG. 1B is a sectional view along section lines B—B of one of the bone plugs of the graft of FIG. 1A;

FIG. 1C is a side elevational view of the graft of FIG. 1A;

FIG. 1D is a sectional view along section lines D—D of one of the bone plugs of the graft of FIG. 1C;

FIG. 2A is a side elevational view of a helical tube saw as is known in the prior art;

FIG. 2B is an axial view of the cutting end of the helical tube saw of FIG. 2A;

FIG. 3A is a side elevational view of a bone plug harvesting instrument according to the present invention;

FIG. 3B is an axial view of the cutting end of the instrument of FIG. 3A;

FIG. 4A is a plan view of a BTB graft obtained with the harvesting instrument of FIG. 3A;

FIG. 4B is a sectional view along section lines B—B of one of the bone plugs of the graft of FIG. 4A;

FIG. 4C is a side elevational view of the graft of FIG. 4A;

FIG. 4D is a sectional view along section lines D—D of one of the bone plugs of the graft of FIG. 4C;

FIG. 5A is a plan view of a first elongated interfitting element of the harvesting instrument of the present invention;

FIG. 5B is an axial view of the cutting end of the first element of FIG. 5A;

FIG. 5C is a detail view of the cutting end of the first element of FIG. 5A;

FIG. 5D is a side elevational view of the first element of FIG. 5A;

FIG. 6A is a plan view of a second elongated interfitting element of the harvesting instrument of the present invention;

FIG. 6B is an axial view of the cutting end of the second element of FIG. 6A;

FIG. 7A is a sectional view along section lines A—A of the second element of FIG. 6A;

FIG. 7B is a sectional view along section lines B—B of the second element of FIG. 6A;

FIG. 7C is a sectional view along section lines C—C of the second element of FIG. 6A;

FIG. 7D is a sectional view along section lines D—D of the second element of FIG. 6A;

FIG. 8A is an exploded view of a bone harvesting kit according to the present invention;

FIG. 8B is an axial view of a typical adapter element for engaging the instrument in a rotatable driver;

FIG. 9 is a plan view of the harvesting instrument in preparation for attachment to a rotatable driver;

FIG. 10A is a front anatomical view of a human knee, showing the relative locations of the femur, tibia, patella and patella tendon;

FIG. 10B is a side elevational view of the knee of FIG. 10A;

FIG. 11 is a front anatomical view of a human knee, in which the portion of the patella tendon which is to be used for the BTB graft is identified and separated from the surrounding patella tendon, and in which is shown the orientation of the second element of the harvesting instrument around the graft portion of the tendon in preparation for harvesting of the graft portion;

Like elements in the respective FIGURES have the same reference numbers.

DETAILED DESCRIPTION OF THE PREFERRED EMBODIMENTS

Figure 12A:
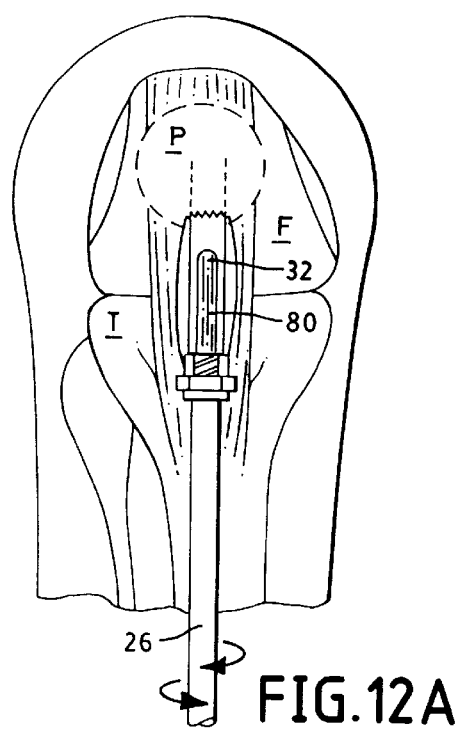
FIG. 12A is a front anatomical view of a human knee, in which a bone plug is being harvested from the patella using the harvesting instrument of the present invention, rotated to show the location of the tendon in the instrument.

In this application, FIGS. 1A–1D illustrate a BTB graft as known in the prior art and having less than fully cylindrical bone plugs. FIGS. 2A–2B illustrates a helical tube saw as known in the prior art for harvesting such bone grafts. FIGS. 4A–4D illustrate a BTB graft having substantially cylindrical bone plugs along substantially their entire length which can be obtained using the bone graft harvesting instrument of the present invention. FIGS. 3A–3B and 5A–9 illustrate the bone graft harvesting instrument of the present invention, and FIGS. 10A–13B illustrate the steps of a method for harvesting a BTB graft using the harvesting instrument of the present invention.

The bone graft harvesting instrument 20 shown in FIG. 3A comprises a generally cylindrical tube 22 which extends along a central axis X between a cutting end 22A and a drive end 22B. A coupler 24 at the drive end of the tube is adapted for releasable engagement with a rotatable driver 26 (shown partially in FIG. 8A). The tube 22 includes first and second elongated interlocking detachable elements 28, 30 which couple together to form a substantially cylindrical body. Each of the elements 28, 30 extends from respective cutting ends 28A, 30A towards respective drive ends 28B, 30B and comprises a portion of the cylindrical tube.

The first element 28 includes the coupler 24 at its drive end 28B. The second element 30 includes an axially extending slot 32 near its drive end 30B.

The first and second elements 28, 30, when interlocked together, form a cutting edge 34 which extends fully about the axis of rotation X, as shown in FIG. 3B.

The coupler 24 is adapted for receiving and lockably engaging with a rotatable driver.

The first element 28 is illustrated in greater detail in FIGS. 5A–5D. As shown in FIGS. 5A and 5D, the first element 28 includes a generally cylindrical shell portion 48 extending along the axis of rotation X from a cutting end 28A to a drive end 28B. The coupler 24 at the drive end is threaded on its outer surface to receive a clamping element 50, such as threaded nut, illustrated in FIGS. 8A and 9. Recessed portions 52 of the coupler are adapted to receive mating extension portions 54 of the second elongated interfitting element 30, as detailed more fully below. The recessed portions 52 include an undercut portion 56 which facilitates locking engagement of the mating extension portions 54 on the second element 30 therein when the first and second elements are coupled together.

As explained in greater detail below, the longitudinally extending edges 55 of the cylindrical shell portion of the first element 28 abut corresponding longitudinally extending edges 57 of the cylindrical shell portion of the second element 30 along substantially the full lengths of the respective elements when they are interlocked to form a cylindrical tube.

The cutting end 28A of the first element includes a bone-cutting region 58, as illustrated in FIGS. 5A–5B and in detail in FIG. 5C. This bone cutting region can include a plurality of sharp serrations, as illustrated in FIG. 5C, or it can be coated with an abrasive coating, such as a diamond coating, for abrading bone and/or soft tissue.

As shown in FIG. 5C, the cutting end 28A includes a shoulder 60 on either side and proximal of the cutting region 58. The shoulders 60 abut corresponding shoulders 62 on the second interfitting element 30 in a hinged engagement when the two elements are coupled together. This hinged engagement interlocks the first and second elements near their respective cutting ends so that the cutting edge 34 extends a full 360° degrees about the axis of rotation of the instrument. The interlocking engagement of the first and second elements ensures that the structural integrity of the cylindrical tube is maintained during use of the harvesting instrument and that the rotational forces on the instrument do not cause the first and second elements to separate.

The coupler 24 includes an axial hole 42 for receiving the shaft portion 38 of the adapter element 36, and a transverse hole 64 for a set screw (not shown) for engaging the shaft portion 38 therein.

The second interfitting element 30 is illustrated in FIGS. 6A–6B. The second element 30 includes a generally cylindrical shell portion 65 which extends along the axis of rotation X between a cutting end 30A and a drive end 30B, as previously described. As shown in FIG. 6A, the drive end 30B of the second element includes a pair of generally cylindrical extension portions 54 which matingly engage with the recessed portions 52 on the first element. In addition, a lip 66 on each of the extension portions 54 engages with the undercut portion 56 on each of the recessed portions 52 on the first element to lockably couple the first and second elements.

The cutting end 30A of the second element includes a cutting region 68 which extends about the axis of rotation X, as shown in FIG. 6B. The respective cutting regions 58, 68 form a circular cutting region 34 which extends a full 360° degrees about the axis X, as shown most clearly in FIG. 3B.

Shoulders 62 on either side and proximal of the cutting region 68 abut against shoulders 60 on the first element in a hinged engagement. In addition, when the first and second elements 28, 30 are interlocked, the respective longitudinally extending edges 55, 57 of the respective cylindrical shell portions 48, 65 abut and are biased towards each other in a mating engagement.

FIGS. 7A–7D illustrate various sections of the second element 30 and, in particular, the profile of the longitudinally extending edges 57 at each of the identified sections. Section A—A (FIG. 7A) shows that the maximum circumference of the cylindrical shell portion is at the cutting region 68. The edges 57A of the cylindrical shell portion at section A—A are tapered as shown to partially surround and grip the corresponding cylindrical shell portion 48 of the first element in a wedge-like fashion, thereby holding the shell portions 48, 65 together.

Section B—B (FIG. 7B) shows the cross-section of the cylindrical shell portion 65 between the cutting region 68 and the end of the axial slot 32. Note that the edges 57B of the cylindrical shell portion 65 do not have the same tapered profile as the edges 57A of the shell portion near the cutting region. Instead, the edges 57B are blunt and provide a maximum bearing surface for the corresponding edges 55 of the first element 28 to abut. As a result of this edge profile, the cylindrical shell portion 48 of the first element 28 pushes against the cylindrical shell portion 65 of the second element 30 and biases the first and second elements towards each other when they are interlocked at the hinge element 61, indicated in FIG. 3B and discussed in greater detail below, near the cutting end. This biased relationship of the first and second elements is critical to provide strength to the tube, maintain its structural integrity during the harvesting procedure, and resist separation forces imparted to the tube during the harvesting operation.

Section C—C (FIG. 7C) shows the cross-section of the cylindrical shell portion 65 in the region of the axial slot 32. The edges 57C of the shell portion 65 in this region are also blunt to provide a maximum bearing surface for the corresponding edges 55 of the cylindrical shell portion 48 of the first element 28. The edges 72 of the axial slot are neither tapered nor blunt but are instead parallel to the horizontal axis Y of the shell portion 65. This design eliminates sharp points on the edges of the slot 32 and thus minimizes trauma to the soft or tendinous tissue that contacts the edges of the slot. In a preferred embodiment, the edges 72 of the axially extending slot may have rounded or beveled tissue-contacting surfaces so that the patella tendon portion of the graft is not abraded or traumatized during the harvesting procedure.

Section D—D (FIG. 7D) shows the cross-section of the cylindrical shell portion 65 of the second element 30 at the drive end. The edges 57D are not adapted for biased engagement with corresponding edges on the shell portion 48 of the first element, as the first and second elements at this end are interlockingly engaged at lip 66, which engages with the undercut portion 56 on each of the recessed portions 52 on the first element.

The first and second elements 28, 30 couple together in three places. The abutting relationship of shoulders 60 on the first element 28 and shoulders 62 on the second element 30 provides the hinge element 61 which establishes a secure engagement of the respective cutting ends to form a circular cutting edge 34 which extends fully about the axis of rotation of the instrument. This hinge element 61 is preferably located near the cutting edge for maximum strength of the cutting surface. As previously discussed, the first and second elements 28, 30 are biasedly engaged along their respective lengths by virtue of the edge profiles of respective longitudinally extending edges 55, 57, which bias the respective shell portions towards each other. In addition, the cylindrical extension portions 54 on the second element 30 and the recessed portions 52 on the first element 28 provides a clamp element 63, indicated in FIG. 3A,which establishes a secure engagement of the respective drive ends of the first and second elements.

It should be noted that the presence of the axial slot 32 opposite from the opening of the cylindrical shell portion 65 of the second element 30 gives the second element a springlike character and permits some degree of compression of the cylindrical extension portions 54 towards each other. In addition, the cylindrical extension portions 54 include a slight outward taper or flare, as shown most clearly in FIG. 6A. When the first and second elements are interlocked, the cylindrical extension portions 54 can be compressed about the coupler 24 of the first element with a clamping element 76, illustrated as a threaded nut in FIGS. 8A and 9, which ensures locking engagement of the first and second elements at the drive end.

FIG. 8A illustrates a kit for harvesting a BTB graft using the harvesting instrument of the present invention. As shown, the harvesting instrument 20 comprises first and second elements 28, 30 interlocked with a clamping element 76 disposed thereon near the drive end of the instrument. An adapter element 36 includes a shaft portion 38 which extends into an axial hole 42 in the coupler 24, and a key portion 40 which extends into a corresponding axial hole 46 in a rotatable driver 26. The driver can be manually operated or powered by conventional means, such as, for example, electricity or compressed air.

In a preferred embodiment, a male-male adapter element 36, shown in FIGS. 8A, 8B and 9, matingly engages with both the coupler 24 and the drive end 26A of a rotatable driver 26. The adapter element 36 can be of any shape which facilitates its engagement with both the coupler and the driver. In the illustrated example, the adapter element 36 includes a shaft portion 38 and a key portion 40. The shaft portion 38 extends from one end of the adapter element and fits within a corresponding opening 42 in the coupler. The shaft portion 38 can include a flat region 44 thereon to prevent rotation of the shaft in the coupler. The key portion 40 extends from an opposite end of the adapter element and is shaped to fit within a corresponding opening 46 in the rotatable driver. In the illustrated embodiment shown in FIG. 8B, the key portion 40 has a triangular cross-section; however, other cross-sections which prevent rotation of the key portion in the driver opening 46 can also be employed.

FIG. 9 illustrates the assembled bone graft harvesting instrument 20, with the clamping element 76 disposed about the drive end of the instrument and compressing the drive end of the second element 30 towards the coupler of the first element 28. Adapter 36 is secured in the instrument via shaft portion 38 and a set screw (not shown) in the coupler. The instrument is now ready to be inserted, via the key portion 38 of the adapter, into a rotatable driver and secured therein in preparation for use.

FIGS. 10A–13B illustrate a method for obtaining a BTB graft having substantially cylindrical bone plugs from a source of living tissue. As shown in FIGS. 10A–10B, the patella tendon 78 typically extends between the tibia T, the patella P and the femur F, with the patella P underlying the tendon, as viewed frontally. As shown in FIG. 11, a section 80 comprising approximately the middle third of the patella tendon is incised longitudinally between its insertion points in the patella and tibia in preparation for harvesting.

An instrument for harvesting a BTB graft having substantially cylindrical bone plugs, as described above, is provided. As shown in FIG. 11, the drive end 30B of the second element 30 of the instrument is manipulated around the tendon graft portion 80 so that the graft portion extends transverse to the axis of the second element and the axially extending slot 32. Because the axial slot in the second element extends from the drive end and terminates some distance from the cutting end, the graft portion 80, when positioned within the slot, is relatively remote from the cutting end 30A of the second element, and thus the risk of inadvertent damage to the graft portion is minimized.

The second element is then oriented longitudinally to be substantially coaxial with the graft portion 80 so as to substantially surround the graft. The first and second elements of the instrument are then interlocked to form a cylindrical tube disposed around the graft portion, as shown in FIG. 12A. The portion of the graft portion 80 which is near the patella P is surrounded by the instrument, which is rotated in FIG. 12A to show the graft portion of the tendon from inside the tube via the axial slot. The portion of the graft 80 near the tibia extends from the axial slot, as shown most clearly in FIG. 12B. The cutting end of the instrument is manipulated to be in contact with the patella P in preparation for harvesting of the patellar bone plug.

The harvesting instrument is then lockably engaged with a rotatable driver 26 by means of an adapter element which matingly engages with both the coupler at the drive end of the tube and the rotatable driver. The harvesting instrument is then reciprocally rotated around and relative to the graft portion 80 at a sufficient speed to form a substantially circular cut in the patella P, with the cut being tangent to the surface of the patella so that the bone plug is substantially circular in cross-section throughout substantially its entire length. The site should be bathed in saline solution as needed to cool the patella and surrounding tissue to minimize trauma from the harvesting procedure.

Figure 12B:
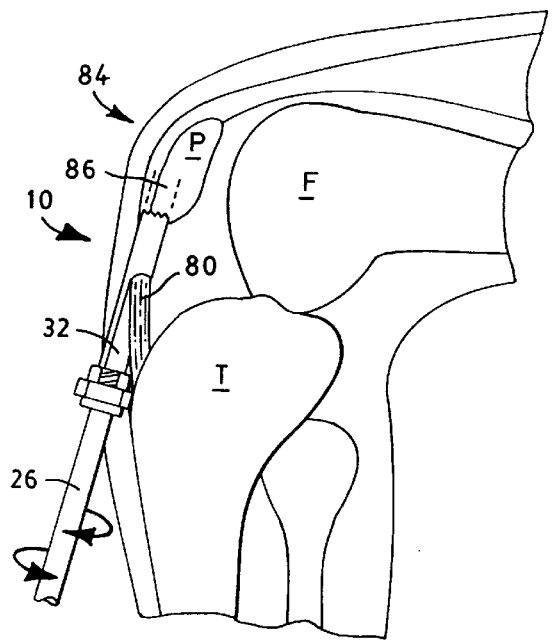
FIG. 12B is a side elevational view of the knee of FIG. 12A, showing the harvesting of the patellar bone plug.

Once the circular cut has been performed to the desired depth in the patella, the bone plug 86 can be detached from the patella by, for example, effecting a transverse cut into the patella at the distal end of the bone plug, as indicated by arrow 84 in FIG. 12B. In one preferred method, the transverse cut is made at this point in the procedure by drilling a series of small holes into the patella in a direction transverse to the axis of the bone plug 86 to approximately the depth of the diameter of the bone plug in order to loosen the bone plug from the patella. Alternatively, the patellar bone plug 86 can remain attached to the patella throughout the remainder of the procedure in which the tibial bone plug is harvested, so that the patellar bone plug is held in place and does not interfere with the tibial bone plug harvesting operation.

The harvesting instrument can then be removed from the rotatable driver, and the first and second elements disengaged from one another, taking care not to damage the tendon portion 80 therein.

Figure 13A:
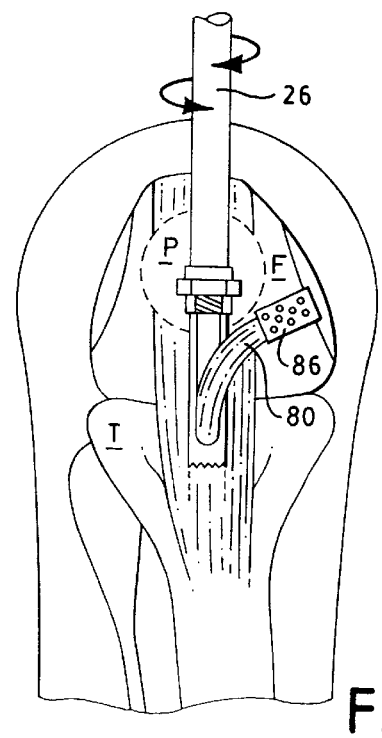
FIG. 13A is a front anatomical view of a human knee, in which a bone plug is being harvested from the tibia using the harvesting instrument of the present invention, rotated to show the location of the tendon in the instrument.
Figure 13B:
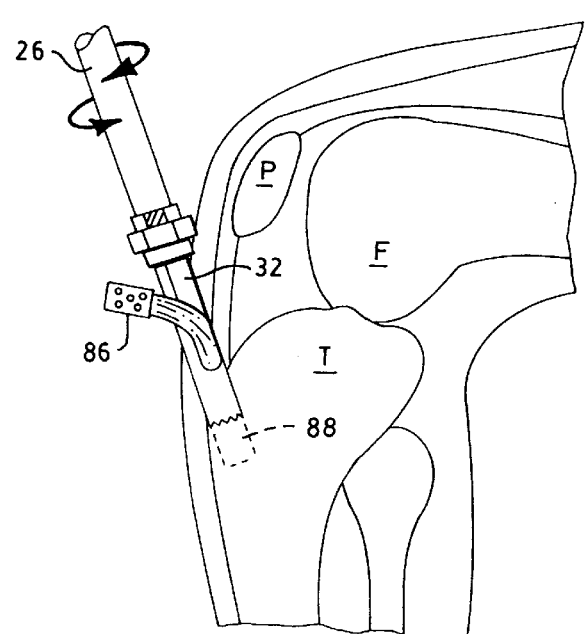
FIG. 13B is a side elevational view of the knee of FIG. 13A, showing the harvesting of the tibial bone plug.

To obtain the tibial bone plug 88, a harvesting instrument of the appropriate size is selected. The second element of the tube is then rotated approximately 180° degrees and reinserted around the graft portion via the axial slot, so that the cutting end is now near the tibia. The first and second elements are once again mutually engaged to form a substantially cylindrical tube disposed around the graft portion. The patellar bone plug 86 and a portion of the tendon graft 80 may now extend from the axial slot in the second element, as shown in FIGS. 13A and 13B, or they may be still attached at the patella. The excised portion of the tendon 80 is surrounded by the instrument, which is rotated in FIG. 13A to show the graft portion of the tendon from inside the tube via the axial slot. The tube is then lockably engaged with the rotatable driver, and the tube is reciprocally rotated around and relative to the graft portion to form a substantially circular cut in the tibia so as to obtain a second substantially cylindrical bone plug therefrom. The site can be bathed in saline to minimize tissue trauma and maintain hydration during the harvesting process. As with the patella, the instrument is manipulated to initiate a cut into the bone which is tangent to the bone surface to obtain a bone plug having a substantially circular cross-section throughout substantially its entire length.

When the cut has reached the desired depth in the tibia, the bone plug 88 can be removed from the surrounding portion of the tibia by conventional means. The resulting patellar and tibial bone plugs 86, 88 are substantially cylindrical and are joined by the excised portion 80 of the patella tendon.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

We claim:

1. An instrument for harvesting a bone-patella tendon-bone graft having bone plugs which are substantially cylindrical for substantially their entire length, said instrument comprising a substantially cylindrical tube extending along a central axis between a cutting end and a drive end, said tube including first and second elongated interlocking detachable elements, each of said elements including an elongated cylindrical shell portion extending from said cutting end toward said drive end, wherein said first and second elements, when interlocked, are biased towards each other and establish a cutting edge extending fully about said axis, wherein said first element includes a coupler at said drive end adapted for releasable engagement with a rotatable driver, and wherein said second element includes an axially extending slot near said drive end.

2. The instrument of claim 1, wherein said cylindrical tube further comprises hinge means disposed near said cutting end of said tube, and biasing means disposed between said cutting end and said drive end of said tube, said hinge means being adapted for hingedly interlocking said first and second elements together near said cutting end, and said biasing means being adapted for biased engagement of said first and second elements along their respective lengths between said cutting end and said drive end of said tube.

3. The instrument of claim 2, wherein said biasing means comprises a set of corresponding contact surfaces on the first and second elements which are adapted for biased engagement with each other to provide an interlocking engagement of the first and second elements substantially along their respective lengths.

4. The instrument of claim 3, further comprising clamping means disposed near the drive end of said tube, wherein said clamping means is adapted for releasably securing said first and second elements together near said drive end.

5. The instrument of claim 3, wherein said cutting end of said tube includes a plurality of bone-cutting teeth.

6. The instrument of claim 3, wherein said cutting end of said tube includes a boneabrading surface.

7. The instrument of claim 6, wherein said bone-abrading surface includes a diamond coating.

8. A kit for harvesting a bone-patella tendon-bone graft having bone plugs which are substantially cylindrical for substantially their entire length, said kit comprising:

A. an instrument for harvesting a bone-patella tendon-bone graft having substantially cylindrical bone plugs, said instrument comprising a substantially cylindrical tube extending along a central axis between a cutting end and a drive end, said tube including first and second elongated interlocking detachable elements, each of said elements including an elongated cylindrical shell portion extending from said cutting end toward said drive end, wherein said first and second elements, when interlocked, are biased towards each other and establish a cutting edge extending fully about said axis, wherein said first element includes a coupler at said drive end adapted for releasable engagement with a rotatable driver, and wherein said second element includes an axially extending slot near said drive end; and B. a rotatable driver adapted for releasable engagement with said coupler.

9. The kit of claim 8, wherein said cylindrical tube further comprises hinge means disposed near said cutting end of said tube, and biasing means disposed between said cutting end and said drive end of said tube, said hinge means being adapted for hingedly interlocking said first and second elements together near said cutting end, and said biasing means being adapted for biased engagement of said first and second elements along their respective lengths between said cutting end and said drive end of said tube.

10. The kit of claim 9, wherein said biasing means comprises a set of corresponding contact surfaces on the first and second elements which are adapted for biased engagement with each other to provide an interlocking engagement of the first and second elements substantially along their respective lengths.

11. The kit of claim 10, further comprising clamping means disposed near the drive end of said tube, wherein said clamping means is adapted for releasably securing said first and second elements together near said drive end.

12. The kit of claim 9, wherein said rotatable driver is adapted for manual and powerdriven oscillatory rotation.

* * * * *